US011814557B2

(12) United States Patent
Widders et al.

(10) Patent No.: US 11,814,557 B2
(45) Date of Patent: Nov. 14, 2023

(54) FATTY ACID AND ROSIN ACID ESTER COMPOSITIONS FOR USE AS PLASTICIZERS IN ADHESIVE FORMULATIONS AND ASSOCIATED METHODS OF USE

(71) Applicant: INGEVITY SOUTH CAROLINA, LLC, North Charleston, SC (US)

(72) Inventors: John C. Widders, Mount Pleasant, SC (US); Russ N. Fitzgerald, Mount Pleasant, SC (US); Olivia J. Jobes, Charleston, SC (US); Brett A. Neumann, Mount Pleasant, SC (US)

(73) Assignee: INGEVITY SOUTH CAROLINA, LLC, North Charleston, SC (US)

( * ) Notice: Subject to any disclaimer, the term of this patent is extended or adjusted under 35 U.S.C. 154(b) by 1004 days.

(21) Appl. No.: 16/082,138

(22) PCT Filed: Mar. 6, 2017

(86) PCT No.: PCT/US2017/021002
§ 371 (c)(1),
(2) Date: Sep. 4, 2018

(87) PCT Pub. No.: WO2017/152188
PCT Pub. Date: Sep. 8, 2017

(65) Prior Publication Data
US 2023/0028097 A1 Jan. 26, 2023

Related U.S. Application Data

(60) Provisional application No. 62/303,615, filed on Mar. 4, 2016.

(51) Int. Cl.
*C09J 193/04* (2006.01)

(52) U.S. Cl.
CPC ................... *C09J 193/04* (2013.01)

(58) Field of Classification Search
CPC ....................................................... C09J 193/04
USPC ........................................................... 524/315
See application file for complete search history.

(56) References Cited

U.S. PATENT DOCUMENTS

| 2,577,734 | A | * | 12/1951 | Brinker | ................... C08L 31/04 |
| | | | | | 428/514 |
| 3,470,212 | A | | 9/1969 | Van Tuyle | |
| 5,120,781 | A | * | 6/1992 | Johnson, Jr. | ............ C08L 53/02 |
| | | | | | 524/274 |
| 6,562,888 | B1 | * | 5/2003 | Frihart | ...................... C09F 1/04 |
| | | | | | 524/270 |
| 8,796,377 | B2 | | 8/2014 | Ag | |
| 2010/0092703 | A1 | | 4/2010 | Fouquay et al. | |
| 2012/0322969 | A1 | | 12/2012 | Sato et al. | |
| 2014/0262016 | A1 | | 9/2014 | Celanese | |
| 2016/0122607 | A1 | * | 5/2016 | Pernecker | .............. C09J 107/00 |
| | | | | | 524/270 |

FOREIGN PATENT DOCUMENTS

| EP | 0854842 | 12/2003 |
| WO | WO2016/115257 | 7/2016 |

OTHER PUBLICATIONS

International Search Report and Written Opinion from PCT/US2017/021002, dated Jun. 14, 2017.

* cited by examiner

*Primary Examiner* — Hui H Chin
(74) *Attorney, Agent, or Firm* — Bryan D. Zerhusen; Nicholas R. Herrel; CANTOR COLBURN LLP

(57) ABSTRACT

The present description provides esterified fatty acid and/or tall oil compositions and their use as alternative plasticizers in adhesives formulations. These esters demonstrate similar or improved performance over adhesives industry standard plasticizers. The description also provides methods of manufacturing and using the same, for example, to improve or modify the performance of adhesive materials, such as, hot melt pressure sensitive adhesives and hygienic adhesives.

18 Claims, 4 Drawing Sheets

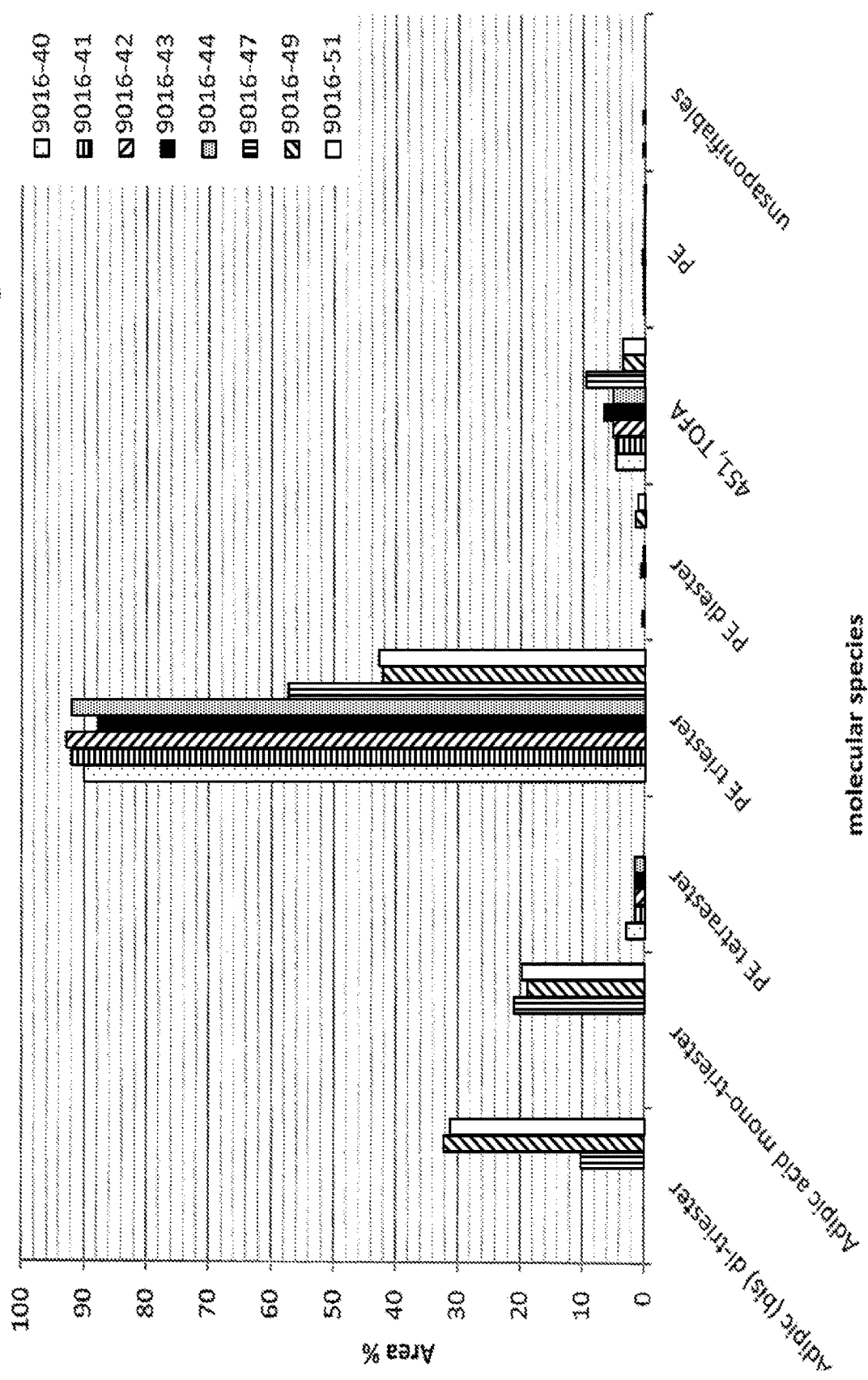

FATTY ACID AND ROSIN ACID ESTER COMPOSITIONS FOR USE AS PLASTICIZERS IN ADHESIVE FORMULATIONS AND ASSOCIATED METHODS OF USE

CROSS-REFERENCE TO RELATED APPLICATIONS

This application is a National Stage Application of PCT/US17/21002, filed 6 Mar. 2017, titled FATTY ACID AND ROSIN ACID ESTER COMPOSITIONS FOR USE AS PLASTICIZERS IN ADHESIVE FORMULATIONS AND ASSOCIATED METHODS OF USE, which claims the benefit and priority to U.S. Provisional Patent Application Ser. No. 62/303,615, titled: Fatty Acid and Rosin Acid Ester Compositions for Use as Plasticizers in Adhesive Formulations and Associated Methods of Use, filed Mar. 4, 2016, all of which are incorporated herein by reference in their entirety for all purposes.

BACKGROUND

1. Field of the Discovery. The description provides compositions of tall oil derivative-based esters for use as an additive, e.g., plasticizer, in adhesive formulations, including but not limited to, hot melt pressure sensitive adhesive formulations and hygienic adhesive formulations.

2. Background Information. To improve or modify the performance characteristics of industrial adhesives, e.g., plasticity, fluidity, viscosity etc., modifying agents, such as plasticizers, can be added. For example, plasticizers can be added to hot melt pressure sensitive adhesives (HMPSA) for use in articles such as adhesive tape to use on a surface such as fabric or skin, and hygienic adhesives for use in articles such as feminine napkins, diapers, tapes and bandages, in order to modify and enhance their performance characteristics.

Pressure sensitive adhesives are a unique class of adhesives characterized by their ability to form bonds when light pressure is applied, additives such as plasticizers can play a key role in the formulation to enhance performance. HMPSAs are unique because they do not solidify to form a hard material; they remain tacky and have the ability to wet-out substrates on contact. Some of the desired properties of hot melt adhesives include low-temperature flexibility, high adhesion strength, wettability, water-resistance, optical clarity, and the ability to accept a wide variety of modifications and additives (See US 20140262016 A1, which is incorporated herein by reference). Plasticizers are blended in the hot melt pressure sensitive adhesive for the purposes of reducing the melt viscosity, providing flexibility and improving the wetting property. Addition of plasticizers also reduces cost, improves pressure-sensitive tack, decrease hardness, and improve low-temperature flexibility.

HMPSAs are widely used in industry and are employed for example in the packaging industry for labeling and packaging, for attaching transport dockets, for the temporary fastening of disposable articles. They are also used for manufacturing articles such as feminine napkins, diapers, tapes, and bandages. However, flaws of exsisting formulations of hot melt pressure sensitive adhesives are frequently observed, for example, insufficient bonding of difficult substrates, incomplete peel or insufficient tensile strength at high and low temperatures. Also, when film substrates are adhesively bonded to solid supports, sometimes creases or waves are created in the film, which disrupts the appearance of such adhesive bonds. Different types of plasticizers may be employed in order to achieve better pressure sensitive properties.

Thus, a need exists in the art to provide additives, e.g., plasticizers, for use in industrial adhesives, such as, pressure sensitive adhesives and HMPSAs, in order to improve their properties.

SUMMARY

The present description relates to esters of a tall oil derivative (e.g., tall oil fatty acid (TOFA) and/or tall oil rosin (TOR)), and at least one polyhydric alcohol. In particular, the tall oil derivative-based esters as described herein are surprisingly and unexpectedly advantageous for use as plasticizers in adhesive formulations, including but not limited to hot melt pressure sensitive adhesive (HMPSA) formulations and hygienic adhesive formulations. The tall oil derivative-based esters as described herein provide similar or improved performance over adhesives industry standard plasticizers, such as, e.g., naphthenic, paraffinic, and mineral oils. The plasticizers as described herein surprisingly and unexpectedly demonstrate one or more benefitial characteristics in adhesive media, including decreased viscosity, increased workability, increased peel, increased loop tack, increased adhesion, suitable shear adhesion failure temperature (SAFT), increased static shear, increased cohesion, and suitable color as compared to adhesives industry standard plasticizers, such as naphthenic, paraffinic, and mineral oils.

Therefore, in one aspect, the description provides a plasticizer comprising an ester of a tall oil derivative, and at least one polyhydric alcohol (e.g., sugar alcohol, polyalcohol, alditol, or glycitol). In certain embodiments, the tall oil derivative is a TOFA, a TOR or a combination thereof. In additional embodiments, the ester is a diester including TOFA, TOR or a combination thereof. In further embodiments, the plasticizer comprises a plurality of ester-linked tall oil derivative moieties coupled to a polyhydric alcohol.

In certain embodiments, the plasticizer comprises a diester of a tall oil derivative and 1,4-Cyclohexanedimethanol (CHDM). In additional embodiments, the plastizer tall oil derivative is a TOFA, a TOR or a combination thereof. In an exemplary embodiment, the plasticzer comprises a diester of 1,4-CHDM and TOFA. In another embodiment, the plastizer comprises a diester of 1,4-CHDM and a TOR. In still additional embodiments, the plasticizer comprises a diester of 1,4-CHDM and a combination of TOFA and TOR. In certain embodiments, the tall oil derivative is modified or fortified. In certain examples the tall oil derivative is maleated.

In another aspect, the description provides a plasticizer composition comprising a plasticizer as described herein, and at least one additional additive. In certain embodiments, the plasticizer composition comprises a mixture of two or more tall oil ester plasticizers as described herein, including diesters of tall oil derivatives as described herein. In any of the embodiments described herein, the respective esterified tall oil derivative-based plasticizers as described herein can be present in the mixture at a relative amount of from 0 to 100% wt, including all values in between.

In an exemplary embodiment, the plasticizer composition comprises a mixture of a 1,4-CHDM TOFA diester, and a 1,4-CHDM TOR diester. In an additional embodiment, the plasticizer composition comprises a mixture of a 1,4-CHDM TOFA diester, and a 1,4-CHDM TOR diester present at a relative ratio of 1:1. In an additional embodiment, the plasticizer composition comprises a 50/50 mixture of a 1,4-CHDM TOFA diester, and a 1,4-CHDM TOR diester.

In any of the aspects or embodiments described herein, the adhesivecomposition can include a tackifier resin.

In any of the aspects or embodiments described herein, the adhesivecomposition can include a copolymer.

In another aspect, the description provides adhesive formulations comprising at least one plasticizer as described herein. In certain embodiments, the description provides a hot melt pressure senstitive adhesive formulation comprising an effective amount of at least one plasticizer as described herein. In additional embodiments, the description provides a hygienic adhesive formulation comprising an effective amount of at least one plasticizer as described herein. In certain embodiments, the plasticizers as described herein are generally comprised in the pressure sensitive hot melt adhesive at a concentration of from about 5 to about 40 wt. %, preferably in a concentration of from about 10 to about 30 wt. %.

In certain embodiments, the adhesive formulation comprises at least one plasticizer as described herein, and at least one of an antioxidant, a tackifier, a copolymer or a combination thereof.

In another aspect, the description provides an adhesive formulation comprising a plasticizer or plasticizer composition as described herein in combination with at least one additional plasticizer. For example, suitable plasticizers are medicinal white oils, naphthenic mineral oils, adipates, polypropylene oligomers, polybutene oligomers, polyisoprene oligomers, hydrogenated polyisoprene and/or polybutadiene oligomers, benzoate esters, vegetal or animal oils and their derivatives, sulfonic acid esters, mono or polyhydric alcohols, polyalkylene glycols having a molecular weight of 200 to 6000 g/mol, such as polypropylene glycol or polybutylene glycol, hydrocarbon oils, polybutene/polyisoprene oligomers, hydrogenated naphthenic oils, vegetal oils or a combination thereof.

In another aspect, the description provides a method for the synthesis of an esterified tall oil derivative-based plasticizer as described herein. In a preffered embodiment, the method for the preparation comprises the steps of: a) heating tall oil derivative, e.g., TOFA, TOR or combination thereof under nitrogenous conditions; b) admixing and stirring in 1,4-cyclohexanedimethanol (CHDM) with heat, optionally followed by addition of at least one catalyst; c) allowing the mixture to reach reaction temperature and reacting to a predetermined acid value; d) allowing the reaction to reach a lower temperature and adding a tall oil derivative, e.g., TOFA, TOR or combination thereof; e) reheating the mixture to desired reaction temperature until a desired acid number value is achieved; and f) retooling the mixture and adding at least one antioxidant.

The preceding general areas of utility are given by way of example only and are not intended to be limiting on the scope of the present disclosure and appended claims. Additional objects and advantages associated with the compositions, methods, and processes of the present invention will be appreciated by one of ordinary skill in the art in light of the instant claims, description, and examples. For example, the various aspects and embodiments of the invention may be utilized in numerous combinations, all of which are expressly contemplated by the present description. These additional advantages, objects and embodiments are expressly included within the scope of the present invention. The publications and other materials used herein to illuminate the background of the invention, and in particular cases, to provide additional details respecting the practice, are incorporated by reference.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating an embodiment of the invention and are not to be construed as limiting the invention. Further objects, features and advantages of the invention will become apparent from the following detailed description taken in conjunction with the accompanying figures showing illustrative embodiments of the invention, in which:

FIG. 5. GPC chromatograms of the TOFA-based plasticizers.

DETAILED DESCRIPTION

Figure 1:
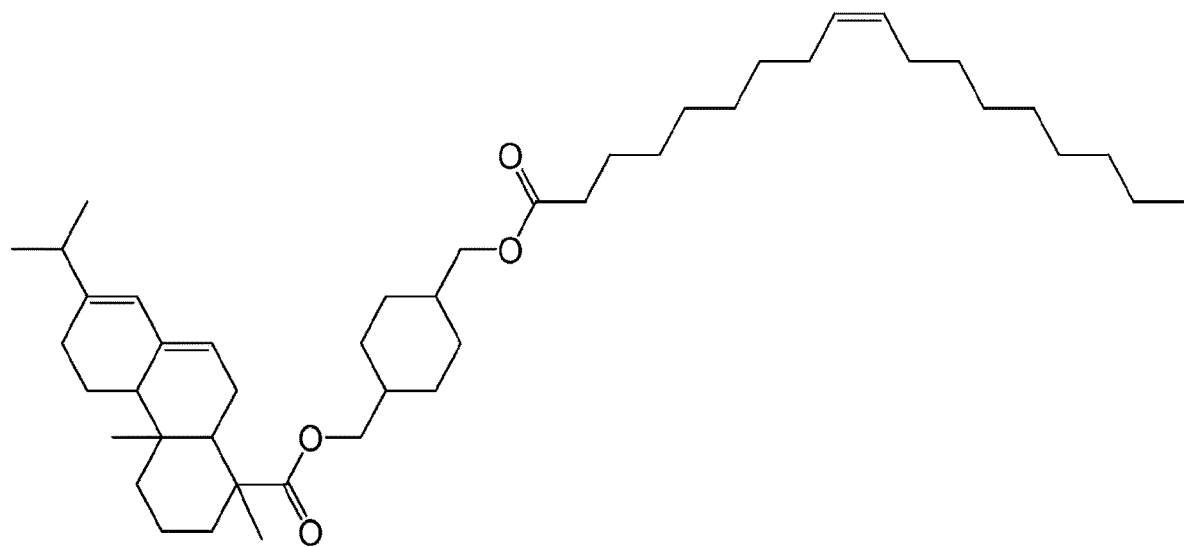
FIG. 1. Exemplary rosin, 1,4 cyclohexanedimethanol, fatty acid.

The following is a detailed description provided to aid those skilled in the art in practicing the present invention. Those of ordinary skill in the art may make modifications and variations in the embodiments described herein without departing from the spirit or scope of the present disclosure. All publications, patent applications, patents, figures and other references mentioned herein are expressly incorporated by reference in their entirety.

Presently described are compositions and methods that relate to the surprising a discovery that the tall oil derivative-based ester plasticizer compositions as described herein demonstrate improved performance. In particular, when formulated into adhesive media, the ester plasticizers as described herein demonstrate one or more of decreased viscosity, increased workability, increased peel, increased loop tack, increased adhesion, suitable SAFT, increased static shear, increased cohesion, and suitable color when compared to adhesives industry standard plasticizers. As such, the description also provides formulations comprising a novel ester as described herein, and an adhesive media, and methods of preparing the same.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

The following terms are used to describe the present invention. Unless otherwise defined, all technical and scientific terms used herein have the same meaning as commonly understood by one of ordinary skill in the art to which this invention belongs. The terminology used in the description is for describing particular embodiments only and is not intended to be limiting of the invention.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

The term "compound", as used herein, unless otherwise indicated, refers to any specific chemical compound disclosed herein and includes tautomers, regioisomers, geometric isomers, and where applicable, stereoisomers, including optical isomers (enantiomers) and other steroisomers (diastereomers) thereof, as well as salts and derivatives thereof where applicable, in context. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. It is noted that in describing the present compounds, numerous substituents and variables associated with same, among others, are described. It is understood by those of ordinary skill that molecules which are described herein are stable compounds as generally described hereunder.

The term "effective" or "effective amount" is used to describe an amount of a compound, composition or component which, when used within the context of its intended use, is sufficient to effectuate an intended result. For example, in certain embodiments, the description provides adhesive formulations comprising an amount of a plasticizer as described herein to improve one or more adhesive properties such as decreased viscosity, increased workability, increased peel, increased loop tack, increased adhesion, suitable SAFT, increased static shear, increased cohesion, and suitable color.

The term "independently" is used herein to indicate that the variable, which is independently applied, varies independently from application to application.

The term "alkyl" refers to an alkyl substituent which is an alkane missing one hydrogen. An acyclic alkyl has the general formula $C_nH_{2n+1}$. A cycloalkyl is derived from a cycloalkane by removal of a hydrogen atom from a ring and has the general formula $C_nH_{2n-1}$. Typically an alkyl is a part of a larger molecule. In structural formula, the symbol R is used to designate a generic (unspecified) alkyl group. The smallest alkyl group is methyl, with the formula $CH_3-$.

The term "benzyl" refers to a $C_6H_5CH_2$ substituent, for example benzyl chloride or benzyl benzoate. The term benzylic is used to describe the position of the first carbon bonded to a benzene or other aromatic ring. For example the molecule, is referred to as a "benzylic" carbocation. The benzyl free radical has the formula $C_6H_5CH_2$. The benzyl carbocation has the formula $C_6H_5CH_2^+$; the carbanion has the formula $C_6H_5CH_2^-$.

The term "glycol" refers to any of a class of organic compounds belonging to the alcohol family; in the molecule of a glycol, two hydroxyl (OH) groups are attached to different carbon atoms. The term is often applied to the simplest member of the class, ethylene glycol. Ethylene glycol, also called 1,2-ethanediol, molecular formula HOCH2CH2OH, is a colourless, oily liquid possessing a sweet taste and mild odour. It is produced commercially from ethylene oxide, which is obtained from ethylene.

Ethylene glycol is widely used as antifreeze in automobile cooling systems and in the manufacture of man-made fibres, low-freezing explosives, and brake fluid. Ethylene glycol and some of its derivatives are mildly toxic. Propylene glycol, also called 1,2-propanediol, resembles ethylene glycol in its physical properties. Unlike ethylene glycol, however, propylene glycol is not toxic and is used extensively in foods, cosmetics, and oral hygiene products as a solvent, preservative, and moisture-retaining agent. Propylene glycol is manufactured in large amounts from propylene oxide, which is obtained from propylene. Other important glycols include 1,3-butanediol, used as a starting material for the manufacture of brake fluids and of plasticizers for resins; 1,4-butanediol, used in polyurethanes and in polyester resins for coatings and plasticizers, and for making butyrolactone, a valuable solvent and chemical intermediate; 2-ethyl-1,3-hexanediol, an effective insect repellent; and 2-methyl-2-propyl-1,3-propanediol, made into meprobamate, a widely used tranquillizing drug.

The term "fatty acids" refers to carboxylic acids derived from or contained in an animal or vegetable fat or oil. Fatty acids are composed of a chain of alkyl groups containing from about 4 to about 22 carbon atoms (usually even numbered) and have a terminal carboxylic acid group. Fatty acids may be straight or branched, saturated or unsaturated and even aromatic. One of the fatty acids used in the present invention is tall oil fatty acid (TOFA), which is predominantly a mixture of oleic acid (~45 wt. %) and linoleic acid (~36 wt. %) and other fatty acids. (EP 0854842 B1).

The term "aliphatic acids" refers to acids of nonaromatic hydrocarbons, such as acetic, propionic, and butyric acids.

The term "rosin acids" refers to mixtures of several related carboxylic acids such as abietic acid, neoabietic acid, dehydroabietic acid, palustric acid, levopimaric acid, pimaric acid and isopimaric acids found in tree resins. Nearly all resin acids have the same basic skeleton: three fused ring fused with the empirical formula $C_{19}H_{29}COOH$.

The term "modified rosin acids" refers to rosin acids chemically modified by a modification such as esterification, hydrogenation, dimerization, functionalization, or any combination thereof.

The present description relates to esters of a tall oil derivative (e.g., tall oil fatty acid (TOFA) and/or tall oil rosin (TOR)), and at least one polyhydric alcohol. In particular, the tall oil derivative-based esters as described herein are surprisingly and unexpectedly advantageous for use as plasticizers in adhesive formulations, including but not limited to hot melt pressure sensitive adhesive (HMPSA) formulations and hygienic adhesive formulations. The tall oil derivative-based esters as described herein provide similar or improved performance over adhesives industry standard plasticizers, such as, e.g., naphthenic, paraffinic, and mineral oils. The plasticizers as described herein surprisingly and unexpectedly demonstrate one or more benefitial characteristics in adhesive media, including decreased viscosity, increased workability, increased peel, increased loop tack, increased adhesion, suitable SAFT, increased static shear, increased cohesion, and suitable color as compared to adhesives industry standard plasticizers, such as naphthenic, paraffinic, and mineral oils (see Table 1 below).

In particular, surprisingly it was found that the plasticizers as described herein demonstrate one or more benefitial characteristics in adhesive media, including decreased viscosity, increased workability, increased peel, increased loop tack, increased adhesion, suitable SAFT, increased static shear, increased cohesion, and suitable color as compared to adhesives industry standard plasticizers, such as naphthenic, paraffinic, and mineral oils.

Therefore, in one aspect, the description provides a plasticizer comprising an ester of a tall oil derivative, and at least one polyhydric alcohol. In certain embodiments, the tall oil derivative is a TOFA, a TOR or a combination thereof. In additional embodiments, the ester is a diester including TOFA, TOR or a combination thereof. In further embodiments, the plasticizer comprises a plurality of ester-linked tall oil derivative moieties coupled to a polyhydric alcohol.

In certain embodiments, the polyhydric alcohol includes, but is not limited to, glycol, polyglycol, glycerine, neopentyl glycol, sorbitol, pentaerythritol, 1,4-cyclohexanedimethanol, 1,4-benzenedimethanol, or a combination thereof. In additional embodiments, the polyhydric alcohol is 1,4-cyclohexanedimethanol (1,4-CHDM).

In certain embodiments, the plasticizer comprises a diester, triester or polyester of a tall oil derivative and 1,4-CHDM. In additional embodiments, the plastizer tall oil derivative is a TOFA, a TOR or a combination thereof. In an exemplary embodiment, the plasticizer comprises a diester of 1,4-CHDM and TOFA. In another embodiment, the plastizer comprises a diester of 1,4-CHDM and a TOR. In still additional embodiments, the plasticizer comprises a diester of 1,4-CHDM and a combination of TOFA and TOR.

In certain embodiments, the plasticizer comprises tall oil rosin (TOR):TOFA:1,4-cyclohexanedimethanol esters, TOFA:TOR:Glycerine, TOFA:TOR:Trimethylolpropane (TMP), TOFA:TOR:diethylene glycol, TOFA:pentaerythritol esters, TOFA:adipic acid: pentaerythritol esters, TOFA: benzyl alcohol esters, hydrogenated rosin acid:stearic acid: 1,4-cyclohexanedimethanol esters, highly branched fatty acid: pentaerythritol, stearic acid: 1,4-cyclohexanedimethanol:disproportionated rosin, TOFA:D-sorbitol, oleic acid: 1,4-cyclohexanedimethaol:TOR, TOFA:1,4-butanediol: TOR, TOFA:1,4-benzenedimethanol:TOR, TOFA:bis[4-(2-hydroxyethoxy)phenyl]sulfone:TOR, and combinations thereof.

TABLE 1

Raw Materials Used in Adhesives.

| Raw Material | Comment | Chemistry | Supplier | Attributes |
| --- | --- | --- | --- | --- |
| Soybean Oil | Competitive Example 1 | Soybean oil | | |
| Calsol 5550 | Competitive Example 2 | Napthenic Oil | Calumet Specialty Product Polymers | Viscosity, SUS @ 210° F. = 56.3 |
| Indopol H300 | Competitive Example 3 | Polybutene | Ineos | Viscosity, SUS @ 100° C. = 2950 (ASTM D2161) |
| Calpar 600 | Competitive Example 4 | Paraffinic Oil | Calumet Specialty Product Polymers | Viscosity, SUS @ 100° F. = 600 (ASTM D2161) |
| Drakeol 34 | Competitive Example 5 | White Mineral Oil | Penreco | Viscosity, SUS@ 100° F. = 370 (ASTM D2161) |

TABLE 1-continued

Raw Materials Used in Adhesives.

| Raw Material | Comment | Chemistry | Supplier | Attributes |
| --- | --- | --- | --- | --- |
| BNX 1037 | Anti-oxidant | 2-methyl-4,6-bis(dodecylthiomethyl)phenol | Mayzo Inc. | White to slightly yellow, waxy solid, Melting Point 28° C. |
| Wingtack Extra | Tackifier | Aromatically modified C5 hydrocarbon | CrayValley | 97° C. Softening Point |
| WestRez 5300 | Tackifier | Rosin ester | MWV | 97° C. Softening Point |
| Escorez 13101C | Tackifier | Aliphatic hydrocarbon | ExxonMobil | Softening point = 93.7° C. |
| Vector 4113A | Polymer | Styrene Isoprene Styrene | TSRC | 15% Styrene, 18% Di-block, Melt Flow Rate = 11 |
| Kraton D1118 | Polymer | Styrene Butadiene Styrene | Kraton | 33% Styrene, 78% Di-block, Melt Index = 10 |
| Kraton D1117 | Polymer | Styrene Isoprene Styrene | Kraton | 17.4% Styrene, 33% Di-block, Melt Index = 33 |

In another aspect, the description provides a plasticizer composition comprising a plasticizer as described herein, and at least one additional additive. In certain embodiments, the plasticizer composition comprises a mixture of two or more tall oil ester plasticizers as described herein, including diesters of tall oil derivatives as described herein. In any of the embodiments described herein, the respective esterified tall oils as described herein can be present in the mixture at a relative amount of from about 0 to 100 wt %, about 1 to 99 wt %, about 5 to 90 wt %, about 10 to 85 wt %, about 20 to 80 wt %, about 30 to 70 wt %, about 40 to 60 wt %, or about 50 wt %, including all values in between.

In an exemplary embodiment, the plasticizer composition comprises a mixture of a 1,4-CHDM TOFA diester, and a 1,4-CHDM TOR diester. In an additional embodiment, the plasticizer composition comprises a mixture of a 1,4-CHDM TOFA diester, and a 1,4-CHDM TOR diester present at a relative ratio of 1:1. In an additional embodiment, the plasticizer composition comprises a 50/50 mixture of a 1,4-CHDM TOFA diester, and a 1,4-CHDM TOR diester.

In any of the aspects or embodiments described herein, the adhesive composition can include a tackifier resin. In certain embodiments, the tackifier resin is a member selected from the group consisting of a rosin, a natural rosin, a modified rosin, a hydrogenated rosin, a glycerol an ester of a natural rosin, a glycerol ester of modified rosin, a pentaerythritol ester of a natural rosin, a pentaerythritol ester of a modified rosin, a pentaerythritol ester of a hydrogenated rosin, a copolymer of a natural terpene, a three-dimensional polymer of a natural terpene, a hydrogenated derivative of a copolymer of a hydrogenated terpene, a polyterpene resin, a hydrogenated derivative of a phenol-based modified terpene resin, an aliphatic petroleum hydrocarbon resin, a hydrogenated derivative of an aliphatic petroleum hydrocarbon resin, an aromatic petroleum hydrocarbon resin, a hydrogenated derivative of an aromatic petroleum hydrocarbon resin, a cyclic aliphatic petroleum hydrocarbon resin, a hydrogenated derivative of a cyclic aliphatic petroleum hydrocarbon resin, and combinations thereof. In certain embodiments, the adhesive composition comprises from about 10 to 90 wt %, about 20 to 80 wt %, about 30 to 70 wt %, about 30 to 60 wt %, about 40 to 60 wt %, or about 50 wt % of a tackifier resin.

In any of the aspects or embodiments described herein, the adhesive composition can include a polymer. In certain embodiments, the polymer is a member selected from the group consisting of ethylene-vinyl acetate (EVA), ethylene-acrylate, Polyolefins, polybutene-1, amorphous polyolefin, polyamides, polyesters, polyurethanes, styrene block copolymers (SBC), polycaprolactone, polycarbonates, fluoropolymers, silicone rubbers, polypyrrole (PPY), styrene-butadiene-styrene (SBS), styrene-ethylene/butylene-styrene (SEBS), styrene-ethylene/propylene (SEP), styrene-isoprene-styrene (SIS), vinyl ethers, conjugated diene compound, vinyl-based aromatic hydrocarbon, hydrogenated conjugated diene-based polymer, non-hydrogenated conjugated diene-based polymer, and combinations thereof. In certain embodiments, the adhesive composition comprises from about 0 to 90 wt %, about 5 to 85 wt %, about 10 to 80 wt %, about 15 to 75 wt %, about 20 to 70 wt %, about 25 to 65 wt %, about 30 to 60 wt % or about 30 to 50 wt % of a polymer.

In certain embodiments, the adhesive composition can include an antioxidant. In certain embodiments, the antioxidant is selected from the group consisting of a phosphite antioxidant, phosphate, phosphonite antioxidant, thioether antioxidant, phenolic antioxidant, hindered aromatic amine, butylated hydroxytoluene, and combinations thereof. In certain embodiments, the adhesive composition comprises from about 0 to 2 wt %, about 0.1 to 1.5 wt %, about 0.5 to 1 wt %, or about 1 wt % of a antioxidant.

In another aspect, the description provides adhesive formulations comprising at least one plasticizer as described herein. The plasticizer is used to adjust, e.g., the viscosity, should provide an improved processability and, if needed, increase the tack of the mixture. In certain embodiments, the description provides a hot melt pressure senstitive adhesive formulation comprising an effective amount of at least one plasticizer as described herein. In additional embodiments, the description provides a hygienic adhesive formulation comprising an effective amount of at least one plasticizer as described herein. In certain embodiments, the plasticizers as described herein are generally comprised in the pressure sensitive hot melt adhesive at a concentration of from about 5 to about 50 wt %, about 10 to about 45 wt %, about 10 to about 40 wt %, or about 10 to about 30 wt %.

In certain embodiments, the adhesive formulation comprises a plasticizer composition including at least one plasticizer as described herein, and at least one of an antioxidant, a tackifier, a copolymer or a combination thereof. In additional embodiments, the adhesive formulation comprises a sufficient amount of a plasticizer composition as described herein to modify or enhance the adhesive properties such as decreased viscosity, increased workability, increased peel, increased loop tack, increased adhesion, suitable SAFT, increased static shear, increased cohesion, and suitable color (i.e., "an effective amount"). In certain embodiments, the plasticizers as described herein are generally comprised in the pressure sensitive hot melt adhesive at a concentration of from about 5 to about 50 wt %, about 10 to about 45 wt %, about 10 to about 40 wt %, or about 10 to about 30 wt %.

In another aspect, the description provides an adhesive formulation comprising a plasticizer or plasticizer composition as described herein in combination with at least one additional plasticizer. For example, suitable plasticizers are medicinal white oils, naphthenic mineral oils, adipates, polypropylene oligomers, polybutene oligomers, polyisoprene oligomers, hydrogenated polyisoprene and/or polybutadiene oligomers, benzoate esters, vegetal or animal oils and their derivatives, sulfonic acid esters, mono or polyhydric alcohols, polyalkylene glycols having a molecular weight of 200 to 6000 g/mol, such as polypropylene glycol or polybutylene glycol, hydrocarbon oils, polybutene/polyisoprene oligomers, hydrogenated naphthenic oils, vegetal oils or a combination thereof. In certain embodiments, the secondary plasticizer as described herein are generally comprised in the pressure sensitive hot melt adhesive at a concentration of from about 0 to about 30 wt %, 0 to about 15 wt %, about 1 to about 25 wt %, about 5 to about 20 wt %, about 10 to about 15 wt % or about 15 wt %.

Hot melt pressure sensitive adhesives generally comprise copolymers as a component of the adhesive, in particular thermoplastic copolymers. The amount of the copolymer should be between from about 5 to about 50 wt %, about 10 to about 45 wt %, about 10 to about 40 wt %, about 10 to about 30 wt % of the hot melt pressure sensitive adhesive. These mostly have a glass transition temperature $T_g$ of less than 0° C. Examples of such polymers encompassed by the adhesive formulations described herein are acrylate, polyester-urethane, ethylene-acrylate, butyl rubber; natural rubber; ethylene-propylene copolymers or styrene copolymers, singly or in mixture, wherein the copolymers concern statistical, alternating, graft or block copolymers. In certain embodiments, the adhesive formulation includes a copolymer selected from the group consisting of styrene block polymers, styrene, styrene-butadiene copolymers (e.g., SBS, SBR), styrene-isoprene copolymers (SIS), styrene-ethylene/butylene copolymers (SEBS), styrene-ethylene/propylene-styrene copolymers (SEPS) or styrene-isoprene-butylene copolymers (SIBS) and combinations thereof. Such products are known to the person skilled in the art and are commercially available.

The amount of the styrene block copolymer should be between 5 and 50 wt. % of the hot melt pressure sensitive adhesive. In particular, the hot melt pressure sensitive adhesive should comprise SIS or SBS polymers. Particularly preferably, it is possible that mixtures of SBS or SIS polymers with SIBS polymers are comprised. These polymers are highly compatible with each other. In one embodiment, the weight ratio of SIBS to styrene block copolymers should be about 1:10 to 2:1, based on the sum of the styrene block copolymers. In certain embodiments, the weight ratio of SIBS to styrene block copolymer is between about 1:5 and 1:1.

Copolymers also comprise ethylene-vinyl acetate copolymers (EVA). Such copolymers are known to the person skilled in the art. They are polymers with a vinyl acetate content of 10 to 40 mol % based on the sum of the monomers. They can optionally comprise additional comonomers. These polymers are usually crystalline or partially crystalline. They have a melting point above 70° C. (measured by DSC). In certain embodiments, the amount of EVA polymer is about 1 to 30 wt %. In certain additional embodiments, the ratio EVA:styrene block copolymers is between about 1:50 to 3:1, or 1:20 to 1:1. It is hypothesized that if the amount of EVA is increased then the cold adhesion will be negatively influenced.

In certain embodiments of, a hot melt pressure sensitive adhesive comprises at least one tackifying resin as an additional component. The resin affords an additional tackiness. In certain embodiments, the tackifying resin is added in an amount of about 20 to 70 wt %, or 30 to 60 wt %. In particular this concerns resins with a softening point from 70 to 130° C. (ring and ball method, DIN 52011). For example, they are aromatic, aliphatic or cycloaliphatic hydrocarbon resins, as well as modified or hydrogenated versions thereof. Practical examples are: aliphatic or alicyclic petroleum hydrocarbon resins and hydrogenated derivatives thereof. Employable resins in the context of the compositions as described herein comprise hydroabietyl alcohol and its esters, especially its esters with aromatic carboxylic acids such as terephthalic acid and phthalic acid; modified natural resins such as resin acids from balsamic resin, tall oil rosin or wood rosin, e.g. completely saponified balsamic resin or alkyl esters of optionally partially hydrogenated colophonium with low softening points, such as e.g. the methyl esters, diethylene glycol esters, glycerine esters and pentaerythritol esters; terpene resins, in particular terpolymers or copolymers of the terpenes, such as styrene-terpenes, α-methylstyrene-terpenes, phenol-modified terpene resins as well as hydrogenated derivatives thereof; acrylic acid copolymers, preferably styrene-acrylic acid copolymers and resins based on functionalized hydrocarbon resins.

In one embodiment, at least one of the ester compositions as described herein can be used as an alternative plasticizer in an adhesive formulation. In another embodiment, at least one of ester plasticizer compositions of the invention can be used as plasticizers in adhesive formulations in a combination with at least one additional plasticizer. For example, suitable plasticizers are medicinal white oils, naphthenic mineral oils, adipates, polypropylene oligomers, polybutene oligomers, polyisoprene oligomers, hydrogenated polyisoprene and/or polybutadiene oligomers, benzoate esters, vegetal or animal oils and their derivatives, sulfonic acid esters, mono or polyhydric alcohols, polyalkylene glycols having a molecular weight of 200 to 6000 g/mol, such as polypropylene glycol or polybutylene glycol, hydrocarbon oils, polybutene/polyisoprene oligomers, hydrogenated naphthenic oils, vegetal oils or a combination thereof.

Minor amounts of waxes may optionally be added to the hot melt pressure sensitive adhesive. The amount should be such that it does not negatively influence the adhesion. The wax can be of natural, chemically modified or of synthetic origin. The amount should be less than 10%. In addition, typical auxiliaries and additives may be incorporated in the hot melt pressure sensitive adhesive according to the invention. Examples of these are stabilizers, antioxidants, such as sterically hindered phenols, phosphites or thioesters, colorants such as titanium dioxide, fillers such as talcum, clay, or coupling agents. Such additives or auxiliaries are usually added to the hot melt pressure sensitive adhesive in quantities up to 5 wt. %, preferably in quantities of about 3 wt. %. Such additives are known to the person skilled in the art. (edited from U.S. Pat. No. 8,796,377 B2)

The present inventivion ester compositions enable hot melt pressure sensitive adhesive formulations that meet or exceed the known in the art adhesives properties such as decreased viscosity, increased workability, increased peel, increased loop tack, increased adhesion, suitable SAFT, increased static shear, increased cohesion, and suitable color In another aspect, the description provides a method for the synthesis of an esterified tall oil derivative-based plasticizer as described herein. In a preffered embodiment, the method for the preparation comprises the steps of: a) heating tall oil derivative, e.g., TOFA, TOR or combination thereof under nitrogenous conditions; b) admixing and stirring in 1,4-cyclohexanedimethanol (CHDM) with heat, optionally followed by addition of at least one catalyst; c) allowing the mixure to reach reaction temperature and reacting to a predetermined acid value; d) allowing the reaction to reach a lower temperature and adding a tall oil derivative, e.g., TOFA, TOR or combination thereof; e) reheating the mixure to desired reaction temperature until a desired acid number value is achieved; and f) recooling the mixure and adding at least one antioxidant.

In another embodiment, the description provides methods of preparation of adhesives comprising the ester compositions as described herein comprising forming an ester plasticizer as described herein, and optionally including an antioxidant, a tackifier, a copolymer or a combination thereof, and admixing the plasticizer composition with an adhesive media.

EXAMPLES

Example 1: Properties of Tall Oil Fatty Acid

Tall oil fatty acid (MWV, Richmond, VA) has typical properties, such as Gardner color of 3 (neat), acid number value of 195 mg KOH/g, and viscosity of 23 centiPoise at 30° C., and is utilized in the exemplary formulations described herein.

Figure 2:
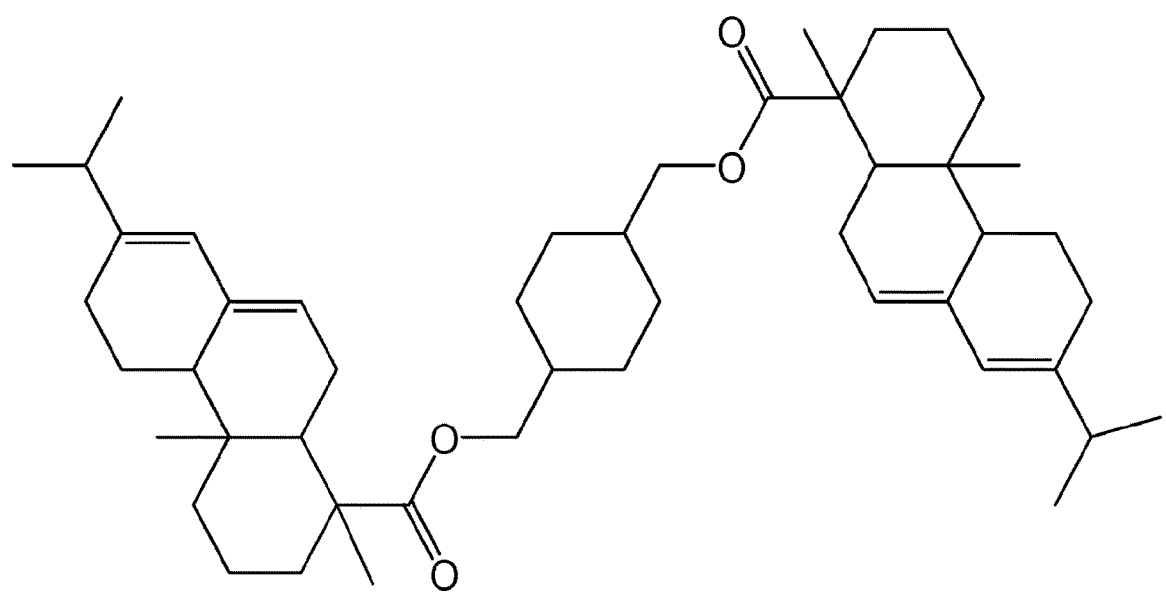
FIG. 2. Exemplary diesters of rosin and 1,4-CHDM.
Figure 3:
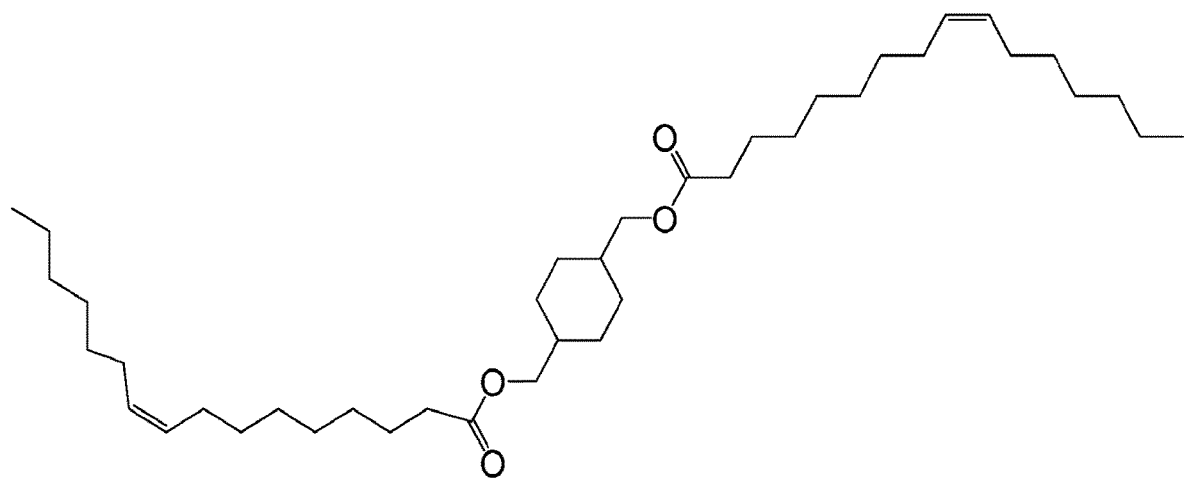
FIG. 3. Exemplary diesters fatty acid and 1,4-CHDM.

Example 2: Examination of the Properties of PE:TOFA Ester and its Reaction Mechanism To a 3 L four-neck round bottom flask equipped with an air driven agitator, condenser, nitrogen sparge tube, and thermocouple was added 89.7% wt of MWV tall oil fatty acid (1435.20 g, 5.08 mol). Under nitrogenous conditions, the tall oil fatty acid was heated to 100° C. over ¼ h followed by the addition of 10.3% wt pentaerythritol (164.80 g, 1.21 mol). The mixture was heated to 235° C. over 4 h and stirred. The mixture reacted for 1.5 h, after which it was cooled to 25° C. Stirring was stopped and the mixture was held for 15 h. The mixture was then heated to 235° C. over 1 h and reacted until an acid number value of 15 mg KOH/g or below was reached. The temperature was decreased to 25° C. The mixture was poured to provide a plasticizer product with typical properties such as Gardner color of 3 (neat), acid number value of <15 mg KOH/g, and viscosity of 82 centiPoise at 30° C. (FIGS. 2a, 2b and 3). Results regarding PE:TOFA Ester adhesive formulation and performance are shown below.

Example 3: Preparation of TOR:TOFA Ester Via 1,4-CHDM

Figure 4:
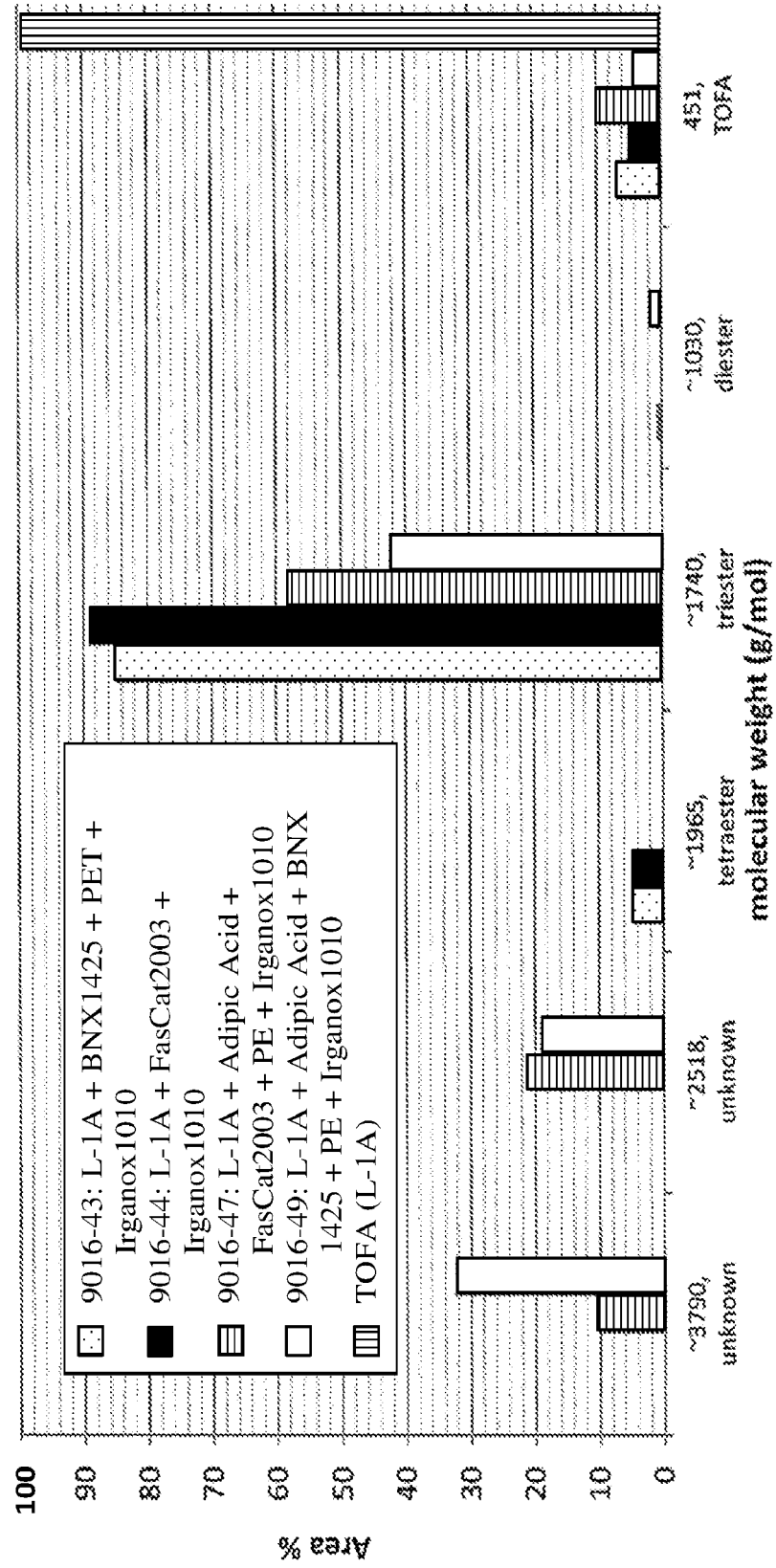
FIG. 4. GPC chromatograms of the TOFA-based plasticizers.

To a 1 L four-neck round bottom flask equipped with an air driven agitator, condenser, nitrogen sparge tube, and thermocouple was added MWV rosin (228.54 g, 0.76 mol). Under nitrogenous conditions, the rosin was heated to 180° C. over 15 minutes followed by the addition of Rosinox™ (1.80 g) and 1,4-cyclohexanedimethanol (116.64 g, 0.81 mol). The mixture was heated to 250° C. over 1.5 h while stirred. To the mixture BNX® 1425 was added (1.80 g, 0.003 mol). The mixture reacted for 2 h, after which the mixture was cooled to 230° C. To the mixture was added MWV tall oil fatty acid (249.72 g, 0.88 mol). The mixture reacted for 2 h, after which it was cooled to 25° C. Stirring was stopped and the mixture was held for 15 h. The mixture was then heated to 275° C. over 3 h and stirred. Upon the mixture reaching 275° C., the mixture reacted until an acid number value of 15 mg KOH/g or below was achieved. Next, the mixture was cooled to 180° C., and Irganox® 1010 (1.50 g, 0.002 mol) was added to the mixture. After 10 minutes, the mixture was poured and cooled to provide a plasticizer product with properties such as Gardner color of 3.7 (neat), acid number value of <15 mg KOH/g, and viscosity of 1480 centiPoise at 30° C. (FIGS. 4, 5 and 6). Results regarding TOR:TOFA Ester via 1,4-CHDM adhesive formulation and performance are shown below.

Example 4: Preparation of TOFA:TOR:Glycerine

To a 500 mL four-neck round bottom flask equipped with an air driven agitator, condenser, nitrogen sparge tube, and thermocouple was added MWV rosin (79.93 g, 0.26 mol). Under nitrogenous conditions, the rosin was heated to 180° C. over 5 minutes followed by the addition of Rosinox™ (0.37 g), BNX® 1425 (0.37 g, 0.0005 mol) and glycerine (37.13 g, 0.40 mol). The mixture was heated to 250° C. over 1 h while stirred. Upon reaching 250° C., the mixture reacted for 3.5 h, after which the mixture was cooled to 220° C. To the mixture was added MWV tall oil fatty acid (148.98 g, 0.53 mol). The mixture reacted for 2.5 h, after which it was cooled to 25° C. Stirring was stopped and the mixture was held for 16 h. The mixture was then heated to 270° C. over 6 h while being stirred. The mixture reacted until an acid number value of 15 mg KOH/g or below was achieved. Next, the mixture was cooled to 150° C., and Irganox® 1010 (0.63 g, 0.0009 mol) was added to the mixture. After 2 minutes, the mixture was poured and cooled to provide a plasticizer product with properties such as Gardner color of 10.3 (neat), acid number value of <15 mg KOH/g, and viscosity of 390 centiPoise at 30° C. (FIGS. 7A and 7b). Results regarding TOFA:TOR:Glycerine adhesive formulation and performance are shown below.

Example 5: Preparation of TOFA:TOR:TMP

To a 500 mL four-neck round bottom flask equipped with an air driven agitator, condenser, nitrogen sparge tube, and thermocouple was added MWV rosin (70.23 g, 0.23 mol). Under nitrogenous conditions, the rosin was heated to 180° C. over 7 minutes followed by the addition of Rosinox™ (0.37 g), BNX® 1425 (0.37 g, 0.0005 mol) and trimethylolpropane (47.55 g, 0.35 mol). The mixture was heated to 245° C. and reacted for 4 h, after which the mixture was cooled to 220° C. To the mixture was added MWV tall oil fatty acid (130.85 g, 0.46 mol). The mixture reacted for 2.75 h, after which it was cooled to 25° C. Stirring was stopped and the mixture was held for 16 h. The mixture was then heated to 275° C. over 4.5 h and stirred. Upon the mixture reaching 275° C., the mixture reacted until an acid number value of 15 mg KOH/g or below was achieved. Next, the mixture was cooled to 230° C., and Irganox® 1010 (0.63 g, 0.0009 mol) was added to the mixture. After 2 minutes, the mixture was poured and cooled to provide a plasticizer product with properties such as Gardner color of 5.2 (neat), acid number value of <15 mg KOH/g, and viscosity of 545 centiPoise at 30° C. (FIG. 8). Results regarding TOFA:TOR:TMP adhesive formulation and performance are shown below.

Example 6. Plasticizers for Use in Non-Wovens and PSAs

Adhesive formulators today use napthenic oils or mineral oils as plasticizers in an adhesive formulation (primarily for PSAs), helping them to tune an adhesive's viscosity. As described herein, plasticizers for adhesives have been created using TOFA as a raw material. It is hypothesized that the polarity of TOFA may increase adhesion, and is a "green" material versus hydrocarbons.

Three different exemplary pentaerythritol-TOFA (L-1A) esters were synthesized. The table below summarizes the reaction conditions and resulting properties. In accordance with the same, in certain embodiments the molar ratio of acid to alcohol is from about 1.2:1 to about 0.5:1. In certain embodiments, the molar ratio of acid to alcohol in the plasticizer are 1.05:1 or 1.17:1.

TABLE 2

Synthesis of exemplary TOFA-based plasticizers

| Notebook-Page | Description | Initial Tofa Color | Final Plasticizer Color | Acid # | Molar Ratio acid:alcohol | Total condensates (mL) | Viscosity at 165° C. (cP) |
|---|---|---|---|---|---|---|---|
|  | TOFA (L-1A) | 2.5 |  | 194.3 |  |  | 2.50 |
| 9016-40 | TOFA + PE | 2.5 | 3.4 | 14.2 | 1.05:1.00 | 72 | 5.25 |
| 9016-41 | TOFA + BNX 1425 + PE + Irganox 1010† | 2.6 | 3.3 | 14.9 | 1.05:1.00 | 70 |  |
| 9016-42 | TOFA + FASCAT 2003 + PE + Irganox 1010 | 2.5 | 4.8 | 12.1 | 1.05:1.00 | 55* |  |

GPC chromatograms of L-1A and the TOFA-based plasticizers were acquired (FIGS. 4 and 5). TOFA L-1A eluted from the columns after 25.1 minutes. TOFA molecular weight is about 282 g/mol. It is believed that esterification did occur upon pentaerythritol addition. This is supported by the appearance of a 1740 MW compound in the three experimental reactions. The reaction can proceed without a catalyst at 235° C., but addition of a catalyst does increase yields of the 1740 MW compound. Use of FasCat 2003 yielded the highest amount of the 1740 MW compound.

Example 7. Plasticizers for Use in Non-Wovens and PSAs

Additional exemplary pentaerythritol-TOFA (L-1A) esters were synthesized. The molar ratio of 1.05 COOH groups 1.00 OH group was used for all reactions, and the maximum reaction temperature was 230° C. The resulting products had higher colors than expected (averaging 4.0). It was hypothesized that using a lower maximum reaction temperature of 200° C. could lower the final average color. The latter two esters have a fraction of the TOFA replaced with adipic acid to build molecular weight and add aliphatic nature. The table below summarizes the reaction conditions and resulting properties.

TABLE 3

Synthesis of exemplary TOFA-based plasticizers.

| Notebook-Page | Description | Initial TOFA Color | Final Plasticizer Color | Acid # | Molar Ratio acid:alcohol | Total condensates (mL) | Viscosity at 30° C. (cP) |
|---|---|---|---|---|---|---|---|
|  | TOFA (L-1A) | 2.5 |  | 194.3 |  |  | 22.5 |
| 9016-43 | TOFA + BNX 1425 + PE + Irganox 1010† | 2.5 | 4.2 | 17.6 | 1.05:1.00 | 49 | 79.5 |
| 9016-44 | TOFA + FASCAT 2003 + PE + Irganox 1010 | 2.5 | 6.0 | 14.9 | 1.05:1.00 | 60 | 80.00 |
| 9016-47 | TOFA + adipic acid + FASCAT 2003 + PE + Irganox 1010 | 2.5 | 6.6 | 27.68 | 1.17:1.00 | 70 | 108.25 |
| 9016-49 | TOFA + adipic acid + BNX 1425 + PE + Irganox 1010 | 2.5 | 5.3 | 14.43 | 1.00:1.00 | 85 | 219.00 |

GPC chromatograms of the TOFA-based plasticizers were acquired (FIGS. 4 and 5). Because the 1740 g/mol peak is present in all the reactions (even those which omit adipic acid), it is hypothesized that this corresponds to the triester formation of TOFA and PE. The theoretical molecular weight of a TOFA:PE triester would be 3(289 g/mol)+1(136 g/mol)−3(18 g/mol)=949 g/mol. Because the 1965 g/mol species is the "heaviest" in the 9016-43/44 reactions, we can assume this peak corresponds to a TOFA:PE tetraester.

It is also hypothesized that peaks 2518 g/mol and 3790 g/mol (present in reactions 9016-47/49) do incorporate the adipic acid in some fashion. It appears that the 3790 g/mol references successful esterification of both acid groups in the adipic acid, whereas the 2518 g/mol species references successful esterification of just one acid group in the adipic acid.

A 48-hour age test at 350° F. was also performed on the following: TOFA (L-1A), 9016-40/41/42/43/44, and Calsol 5550. Charts on color and viscosity change (which were too large to replicate in this space). Take away points from this age test include the following: Calsol 5550 showed the least amount of viscosity change (167 cP to 180 cP); Of the lab batches, those that used BNX 1425 as the esterification catalyst saw less viscosity change than those that used Fascat 2003.

Example 8. Plasticizers for Use in Non-Wovens and PSAs

Eight different batches of exemplary plasticizers were synthesized—five TOFA/pentaerythritol esters and three TOFA/adipic acid/pentaerythritol esters. The chart below summarizes their properties.

GPC chromatograms of all eight TOFA-based plasticizers were acquired. It is hypothesized that the bulk species in the TOFA/pentaerythritol reactions (9016-40 through 9016-44) are TOFA-polyol triesters. The addition of adipic acid in the latter three reactions (901647 through 9016-51) yielded two distinct, heavier species. It is hypothesized that the heaviest of these species is a diester of adipic acid with the free hydroxyl group of the TOFA:PE triesters (see image below).

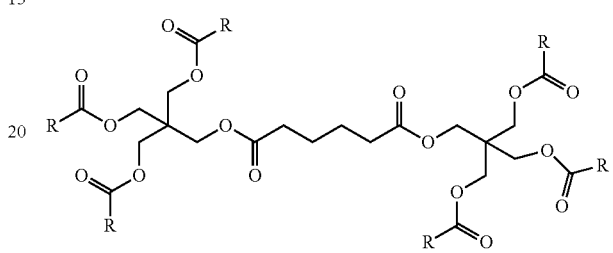

*R represents TOFA moieties

The plot in FIG. 5 summarizes all eight GPC chromatograms for this project. Notice how the addition of adipic acids decreases the presence of the hypothesized triester species and increases the presence of heavier species. The presence of these heavier species is especially noticed in viscosity testing; the latter three reactions show gains in viscosity.

Age testing was performed on several of the plasticizers. Results for 9016-47 and 9016-49 are shown below.

TABLE 4

Properties of exemplary TOFA-based plasticizers.

| Notebook-Page | Description | Color, neat | Acid # | Molar Ratio acid:alcohol | Total condensates (mL) | Viscosity at 30° C. (cP) |
|---|---|---|---|---|---|---|
| | TOFA (L-1A) | 2.5 | 194.3 | | | 22.5 |
| | Calsol 5550 | 0.4 | | | | 166.75 |
| 9016-40 | TOFA + PE | 3.5 | 14.2 | 1.05:1.00 | 72 | 81.5 |
| 9016-41 | TOFA + BNX 1425 + PE + Irganox 1010† | 3.7 | 14.9 | 1.05:1.00 | 70 | 78.25 |
| 9016-42 | TOFA + FASCAT 2003 + PE + Irganox 1010† | 4.9 | 12.1 | 1.05:1.00 | 55 | 79.25 |
| 9016-43 | TOFA + BNX 1425 + PE + Irganox 1010 | 4.2 | 17.6 | 1.05:1.00 | 49 | 79.50 |
| 9016-44 | TOPA + FASCAT 2003 + PE + Irganox 1010 | 6.0 | 14.9 | 1.05:1.00 | 60 | 80.00 |
| 9016-47 | TOFA + adipic acid + FASCAT 2003 + PE + Irganox 1010 | 4.6 | 27.7 | 1.17:1.00 | 70 | 108.25 |
| 9016-49 | TOFA + adipic acid + BNX 1425 + PE + Irganox 1010 | 5.3 | 14.4 | 1.00:1.00 | 85 | 219.00 |
| 9016-51 | TOFA + adipic acid + FASCAT 2003 + PE + Irganox 1010 | 4.8 | 13.6 | 1.00:1.00 | 100 | 209.50 |

TABLE 5

Age testing of exemplary TOFA-based plasticizers

| Notebook Page | Description | Initial color, neat | Final color, neat | Initial viscosity 30° C.(cP) | Final viscosity 30° C. (cP) |
|---|---|---|---|---|---|
| | TOFA (L-IA) | 2.5 | >18 | 22.50 | 80.00 |
| | Calsol 5550 | 0.4 | 15.5 | 166.75 | 179.75 |
| 9016-47 | TOFA + adipic acid + FASCAT 2003 + PE + Irganox ® 1010† | 4.6 | 12.4 | 108.25 | 337.00 |
| 9016-49 | TOFA + adipic acid + BNX 1425 + PE + Irganox 1010 | 5.4 | 12.4 | 219.60 | 332.00 |
| 9616-51 | TOFA + adipic acid + FASCAT 2003 + PE + Irganox 1010 | 4.8 | TBD | 209.50 | TBD |

In certain embodiments, the plasticizer composition as described herein has a final viscosity at 30° C. of from about 75 cP to about 350 cP. In certain embodiments, the final viscosity is from 1 to about 5 times of the initial viscosity.

Example 9. TOFA-Based Plasticizers for Use in Non-Wovens and PSAs

Additional exemplary TOFA-based plasticizer was synthesized—a tall oil fatty acid benzyl ester (9016-67). The chart below includes its properties.

TABLE 6

Comparative properties of exemplary TOFA-based placticizers.

| Notebook Page | Description | Color, neat | Acid # | Molar ratio acid:alcohol | Distillate (mL) | Viscosity at 30° C. (cP) |
|---|---|---|---|---|---|---|
| | TOFA (L-1A) | 2.5 | 194.3 | | | 22.5 |
| | Calsol 5550 (standard) | 0.4 | | | | 166.75 |
| 9016-40 | TOFA + PE | 3.5 | 14.2 | 1.05:1.00 | 72 | 81.5 |
| 9016-41 | TOFA + BNX 1425 + PE + Irganox 1010 | 3.7 | 14.9 | 1.05:1.00 | 70 | 78.25 |
| 9016-42 | TOFA + FASCAT 2003 + PE + Irganox 1010 | 4.9 | 12.1 | 1.05:1.00 | 55 | 79.25 |
| 9016-43 | TOFA + BNX 1425 + PE + Irganox 1010 | 4.2 | 17.6 | 1.05:1.00 | 49 | 79.50 |
| 9016-44 | TOFA + FASCAT 2003 + PE + Irganox 1010 | 6.0 | 14.9 | 1.05:1.00 | 60 | 80.00 |
| 9016-47 | TOFA + adipic acid + FASCAT 2003 + PE + Irganox 1010 | 4.6 | 27.7 | 1.17:1.00 | 70 | 108.25 |
| 9016-49 | TOFA + adipic acid + BNX 1425 + PE + Irganox 1010 | 5.3 | 14.4 | 1.00:1.00 | 85 | 219.00 |
| 9016-51 | TOFA + adipic acid + FASCAT 2003 + PE + Irganox 1010 | 4.8 | 13.6 | 1.00:1.00 | 100 | 209.50 |
| 9016-67 | TOFA + benzyl alcohol + FASCAT 2003 | 6.6 | 4.82 | 0.878:1.00 | 40 | 18.75 |

The theoretical weight of the product is about 373 g/mol (for the oleate species). GPC revealed a molecular weight of 482 g/mol. TOFA, L-1A is 454 g/mol according to the same GPC instrument. 482 g/mol is a sign that we did indeed esterify our TOFA. Below is the structure of the oleate species.

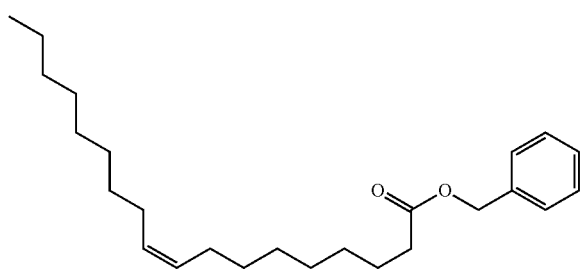 [SMILES: CCCCCCCC/C=C\CCCCCCCC(=O)OCc1ccccc1]

It is unknown whether this plasticizer will favor localization to the mid-block or the end-block of an SIS/SBS polymer system.

Example 10. TOFA-Based Plasticizers for Use in Non-Wovens and PSAs

Two additional TOFA-based plasticizers were synthesized—this time an ester of OCD-128 and pentaerythritol, as well as a mixture of TOR and TOFA esterified with 1,4-cyclohexanedimethanol. The chart below includes their properties.

TABLE 7

Properties of exemplary TOFA-based plasticizers.

| Notebook Page | Description | Color, neat | Acid # | Molar ratio acid:alcohol | Viscosity at 30° C. (cP) |
|---|---|---|---|---|---|
| | TOFA (L-IA) | 2.5 | 194.3 | | 22.5 |
| | Calsol 5550 (standard) | 0.4 | | | 166.75 |
| 9016-40 | TOFA + PE | 3.5 | 14.2 | 1.05:1.00 | 81.5 |
| 9016-41 | TOFA + BNX 1425 + PE + Irganox 1010 | 3.7 | 14.9 | 1.05:1.00 | 78.25 |
| 9016-42 | TOFA + FASCAT 2003 + PE + Irganox 1010 | 4.9 | 12.1 | 1.05:1.00 | 79.25 |
| 9016-43 | TOFA + BNX 1425 + PE + Irganox 1010 | 4.2 | 17.6 | 1.05:1.00 | 79.50 |
| 9016-44 | TOFA + FASCAT 2003 + PE + Irganox 1010 | 6.0 | 14.9 | 1.05:1.00 | 80.00 |
| 9016-47 | TOFA + adipic acid + FASCAT 2003 + PE + Irganox 1010 | 4.6 | 27.7 | 1.17:1.00 | 108.25 |
| 9016-49 | TOFA + adipic acid + BNX 1425 + PE + Irganox 1010 | 5.3 | 14.4 | 1.00:1.00 | 219.00 |
| 9016-51 | TOFA + adipic acid- FASCAT 2003 + PE + Irganox 1010 | 4.8 | 13.6 | 1.00:100 | 209.50 |
| 9016-67 | TOFA + benzyl alcohol + FASCAT 2003 | 6.6 | 4.82 | 0.878:1.00 | 18.75 |
| 9016-76 | OCT-128 + PE + FASCAT 2003 + Irganox 1010 | 12.9 | 10.1 | 1.00:1.00 | 241 |
| 9016-80 | Tall Oil Rosin + 1,4-CHDM + Rosinox → time → + TOFA | 1.8 | <12 | 1.00:1.00 | 1600 |

Example 11. OCD-128+PE

The objective of this experiment was to utilize OCD-128 in place of TOFA, L-1A, and compare its final properties to that of the previously synthesized TOFA, L-1A, +PE esters (ie. 9016-42 & 9016-44). Using OCD-128 and pentaerythritol (PE) at 1.00:1.00 COOH/OH ratio, the reagents were reacted under nitrogenous conditions for about 5 hours at an average of 200° C. until AcV dropped to 11.99. Then, the reaction was cooled and poured. Final AcV was 10.08; viscosity at 30° C. was 241 cP. Gardner color (neat) was 12.9.

Example 12. TOR+1,4-CHDM+TOFA

The objective of this experiment was to link TOR to TOFA via a diol. A diol was selected versus other polyols to keep molecular weight somewhere near that of Calsol. 1,4-cyclohexanediomethanol (CHDM) was chosen in the belief that its bulky, aliphatic center would help shield the polarity of our ester linkages once placed in an adhesive system. Rosinox was added in an attempt to disproportionate the TOR moieties, hence yielding some tetrahydroabietic moieties (ie. naphthenic nature). BNX 1425 was included to aid in esterification and bleach the system.

The COOH/OH ratio for this reaction was 1.00:1.00. Reaction temperature was kept well below CHDM's boiling point, however some loss is assumed. First, the TOR, BNX 1425, Rosinox, and CHDM were reacted under nitrogenous conditions for about 3.5 hours at 250° C. (Aside: In theory, one molecule of TOR would esterify to every one molecule of CHDM, leaving one —OH available per complex. In reality, a mixture of TOR-CHDM and TOR-CHDM-TOR was forming).y Next, TOFA was added and allowed to react for about 3 hours at 230° C. Then, the reaction was cooled and poured. Final AcV was 33.88. GPC results revealed 12% leftover CHDM and 19% left over TOR. Clearly, the TOR was not given enough time or energy to react with the CHDM before adding the TOFA. A high AcV product was undesired, so the material was reheated under nitrogenous conditions for about 6.5 hours at 250° C. Final AcV was −12; viscosity at 30° C. was 1600 cP. Gardner color (neat) was 1.8. GPC results reveal 6.8% unreacted TOR. Three major species emerged as well as a fourth, heavier species.

TABLE 8

Summary of the GPC findings.

| GPC molecular weight (g/mol) | Area % | Species Prediction |
|---|---|---|
| 297 | 6.77 | TOR |
| 642 | 22.72 | TOR-CHDM-TOR |
| 787 | 42.99 | TOR-CHDM-TOFA |
| 1035 | 18.83 | TOR-CHDM-TOFA |
| 1773 | 7.65 | Complexes made via dimer acids |

Example 13. TOFA-Based Plasticizers for Use in Non-Wovens and PSAs

An additional plasticizer was synthesized—a mixture of hydrogenated rosin and stearic acid esterified with 1,4-cyclohexanedimethanol. The chart below includes its properties.

TABLE 9

Comparitive properties of exemplary hydrogenated rosin and stearic acid esterified with 1,4-cyclohexanedimethanol.

| Notebook Page | Description | Color, neat | Acid # | Molar ratio acid:alcohol | Viscosity at 30° C. (cP) |
|---|---|---|---|---|---|
| | TOFA (L-1A) | 2.5 | 194.3 | | 22.5 |
| | Calsol 5550 (standard) | 0.4 | | | 166.75 |
| 9016-40 | TOFA + PE | 3.5 | 14.2 | 1.05:1.00 | 81.5 |
| 9016-41 | TOFA + BNX 1425 + PE + Irganox 1010 | 3.7 | 14.9 | 1.05:1.00 | 78.25 |
| 9016-42 | TOFA + FASCAT 2003 + PE + Irganox 1010 | 4.9 | 12.1 | 1.05:1.00 | 79.25 |
| 9016-43 | TOFA + BNX 1425 + PE + Irganox 1010 | 4.2 | 17.6 | 1.05:1.00 | 79.50 |
| 9016-44 | TOFA + FASCAT 2003 + PE + Irganox 1010 | 6.0 | 14.9 | 1.05:1.00 | 80.00 |
| 9016-47 | TOFA + adipic acid + FASCAT 2003 + PE + Irganox 1010 | 4.6 | 27.7 | 1.17:1.00 | 108.25 |
| 9016-49 | TOFA + adipic acid + BNX 1425 + PE + Irganox 101† | 5.3 | 14.4 | 1.00:1.00 | 219.00 |
| 9016-51 | TOFA + adipic acid- FASCAT 2003 + PE + Irganox 1010 | 4.8 | 13.6 | 1.00:1.00 | 209.50 |
| 9016-67 | TOFA + benzyl alcohol + FASCAT 2003 | 6.6 | 4.82 | 0.878:1.00 | 18.75 |
| 9016-76 | OCT-128 + PE + FASCAT 2003 + Irganox 1010 | 12.9 | 10.1 | 1.00:1.00 | 241 |
| 9016-80 | TOR + 1,4-CHDM + Rosinox → time → + TOFA | 1.8 | <12 | 1.00:1.00 | 1600 |
| 9016-88 | Hydrogenated rosin + 1,4-CHDM → time → stearic acid | 2.9* | 15.2 | 0.832:1.00 | n/a** |

Example 14. Hydrogenated Rosin+1,4-CHDM+Stearic Acid

The objective of this experiment was to synthesize a hydrogenated version of 9016-80. Hence, in our formulation, we replaced TOFA with stearic acid and our SS-A rosin with hydrogenated rosin (Foral AX from Pinova). Our diol, again, was 1,4-cyclohexanedimethanol. The reaction proceeded in exactly the same manner as 9016-80 wherever possible. The goal was to reproduce the same distribution of final species as in 9016-80 but in fully saturated analogues. The reaction stalled on day two, requiring another day of reacting and a back addition of 1,4-CHDM to address the unreacted Foral AX (signaled by a high acid value and GPC).

Example 15. Plasticizers for Use in Non-Woven and PSAs

TOFA L1-A with pentaerythritol to create potential plasticizers/diluents for use in HM PSA and non-woven applications. These materials were formulated into a SIS based HM PSA and were coated into 1 mil films and tested for baseline pressure sensitive performance. Calsol 5550 napthenic process oil is being used as the control plasticizer/diluent in this study. This material is commonly used in numerous pressure sensitive applications. Tables 10 and 11 highlight the details of the various materials that have been produced.

Initial testing shows that each modification of the L1-1 TOFA produces better adhesive properties than straight L1-A. The choice of FastCat 2003 catalyst over BNX 1425 appears to produce products with higher cohesive strength (Static Shear) than the control. When modified with Adipic acid a boost in heat resistance (SAFT) was observed compared to the control. Plasticizer 9016-0049 used FastCat 2003 and a higher level of Adipic acid. The initial adhesive properties obtained with this material show a viscosity and softening point closer to that produced with the control.

TABLE 10

Exemplary Tall Oil Fatty Acid-based ester plasticizer details.

| Lab Notebook Page | Comment | Neat color (Gardner) | Acid # |
|---|---|---|---|
| | TOFA (L-1A) | 2.5 | 194.3 |
| 9016-0040 | TOFA + PE | 3.4 | 14.2 |
| 9016-0041 | TOFA + BNX 1425 + PE + Irganox 1010 | 3.3 | 14.9 |
| 9016-0042 | TOFA + FASCAT 2003 + PE + Irganox 1010† | 4.8 | 12.1 |
| 9016-0047 | TOFA + FASCAT 2003 + PE + Irganox 1010 + adipic acid | 6.6 | 27.68 |
| 9016-0049 | TOFA + FASCAT 2003 + PE + Irganox 1010 + adipic acid at higher % | 5.3 | 14.43 |

TABLE 11

Shows the properties of the adhesives produced using the exemplary samples.

| Lab Notebook # | Plasticizer | Viscosity @ 350° F. (cPs) | Mettler Softening Point (° C.) | 180° Peel-SS (Lbf) | Loop Tack (Lbf) | SAFT (° F.) | Static Shear-Adjusted (Minutes)* |
|---|---|---|---|---|---|---|---|
| 9014-0040 | Calsol 5550 (Control Sample) | 17,325 | 123.1 | 3.9 | 5.0 | 162.5 | 136 |
| 9014-0038 | L1-A | 10,100 | 103.2 | 1.4 | 2.5 | 127.8 | 73 |
| 9020-0004 | 9016-0040 | 12,000 | 109.1 | 2.7 | 3.4 | 126.3 | 103 |
| 9020-0005 | 9016-0041 | 10,950 | 106 | 2.4 | 3.6 | 124.0 | 54 |
| 9014-0039 | 9016-0042 | 9,375 | 108.2 | 2.5 | 3.2 | 126.0 | 234 |
| 9014-0042 | 9016-0047 | 11,125 | 110.2 | 2.9 | 3.6 | 206.7 | 333+ (**) |
| 9014-0043 | 9016-0049 | 15,850 | 113.8 | TBD | TBD | TBD | TBD |

*highest and lowest value tossed out.
**Testing ongoing. Samples have passed 333+ minutes.

TABLE 12

Comparative Properties of Adhesives with exemplary TOFA-based plasticizers and Calsol-5550.

| Adhesive | Plasticizer | Plasticizer Details | Viscosity @ 350° F. (CPS) | Mettler Softening Point (° C.) | 180° Peel-SS (Lbf) | Loop Tack (Lbf) | SAFT (° F.) | Static Shear (Minutes) |
|---|---|---|---|---|---|---|---|---|
| 9014-0040 | Calsol 5550 | | 17,325 | 123.1 | 3.9 | 5.0 | 162.5 | 136 |
| 9014-0038 | L1-A | L1-A | 10,100 | 103.2 | 1.4 | 2.5 | 127.8 | 73 |
| 9020-0004 | 9016-0040 | TOFA + PE | 12,000 | 109.1 | 2.7 | 3.4 | 126.3 | 103 |
| 9020-0005 | 9016-0041 | TOFA + BNX 1425 + PE + Irganox 1010 | 10,950 | 106 | 2.4 | 3.6 | 124.0 | 54 |
| 9014-0039 | 9016-0042 | TOFA + FasCat 2003 + PE + Irganox 1010 | 9,375 | 108.2 | 2.5 | 3.2 | 126.01 | 234 |
| 9014-0042 | 9016-0047 | TOFA + FasCat 2003 + PE + Irganox 1010 + Adipic Acid | 11,125 | 110.2 | 2.9 | 3.6 | 206.69 | 409 |

Example 16. Plasticizers for Use in Non-Woven and PSAs

Modifying TOFA L1-A with pentaerythritol to create potential plasticizers/diluents for use in HM PSA and non-woven applications. These materials were formulated into a SIS based HM PSA and were coated into 1 mil films and tested for baseline pressure sensitive performance. Calsol 5550 napthenic process oil is being used as the control plasticizer/diluent in this study. Lab NB #9014-0051 is the latest attempt at modifying the L1-A TOFA. This material is remake of a previous material but with a catalyst replacement. In this reaction is replacing the catalyst BNX 1425 with FastCat 2003. In previous runs it appeared that the FastCat produced higher levels of static shear and heat resistance in a SIS based pressure sensitive adhesive.

The adhesive made with this material did not illustrate this trend. The adhesive (9014-0046) was low in adhesive peel strength and tack values. During the shear testing the mode of failure was adhesive failure rather than cohesive failure. The static shear test is designed to test the cohesive strength of an adhesive and needs to result in cohesive failure to be considered valid. The test geometry that was used (a tape with a test area of 0.5" wide by 1" long) did not have enough adhesive strength to support the weight (1000 grams) so the adhesive was never truly stressed in a manner that would result in cohesive failure.

The table below highlights the results of testing other adhesive prepared using the TOFA based plasticizers and Calsol 5550 control.

Example 17. Plasticizers for Use in Non-Woven and PSAs (Accelerate Growth)

Modifying TOFA L1-A with pentaerythritol to create potential plasticizers/diluents for use in HM PSA and non-woven applications. These materials were formulated into a SIS based HM PSA and were coated into 1 mil films and tested for baseline pressure sensitive performance. Calsol 5550 napthenic process oil is being used as the control plasticizer/diluent in this study. The most recent sample examined was 9016-0067. This material is based on TOFA modified with benzyl alcohol. The results of the screening are listed below in Table 13.

TABLE 13

Comparative properties of exemplary TOFA ester plasticizers.

| Lab Notebook # | Plasticizer | Rxn-Pathway | Viscosity @ 350° F. (CPS) | Mettler Softening Point (° C.) | 180° Peel-SS (Lbf) | Loop Tack (Lbf) | SAFT (° F.) | Static Shear (1" × 1", 1000 Grams) |
|---|---|---|---|---|---|---|---|---|
| 9014-0040 | Calsol 5550 (control sample) | Control | 17,325 | 123.1 | 3.9 | 5.0 | 163.0 | 8,290 |
| 9023-0019 | 9016-0067 | TOFA + FASTCAT 2003 + benzyl alcohol | 7,400 | 92.7 | 1.4 | 2.3 | 186 | 1,161 |

Based on initial properties the viscosity is lower with the test plasticizer as are peel, loop tack and static shear. While lower viscosity can be a benefit in the application of the adhesive the loss in adhesive properties is not beneficial. The SAFT (heat resistance) with the test material is higher however and that typically is seen as a benefit (see Table 14).

TABLE 14

Comparative properties of exemplary TOFA and napthenic oil blends.

| Lab Notebook # | Plasticizer | Viscosity @ 350° F. (CPS) | Mettler Softening Point (° C.) | 180° Peel-SS (Lbf) | Loop Tack (Lbf) | SAFT (° F.) | Static Shear (1" × 1", 1000 Grams) |
|---|---|---|---|---|---|---|---|
| 9023-0017 | Calsol 5550 | 15,100 | 120.3 | 3.9 | 5.0 | 163.0 | 8,250 |
| 9023-0029 | 50% 9014-0051/50% Calsol 5550 | 18,000 | 122.6 | 2.8 | 4.7 | 211.1 | 1,253 |
| 9023-0030 | 25% 9014-0051/75% Calsol 5550 | 17,950 | 123.3 | 3.0 | 5.2 | 212.1 | 1,275 |
| 9014-0046 | 9016-0051 | 18,875 | 115.9 | 1.2 | 1.8 | 205.52 | 1,161 |

Example 18. Plasticizers for Use in Non-Woven and PSAs

Materials 9016-76 and 9016-80 showed promise and performance equivalent or better than the napthenic oil control. The tables below shows the performance data. These new materials are subjected to 177° C. for 72 hours to better understand their aging characteristics.

TABLE 15

Comparative properties of exemplary plasticizers.

| Plasticizer ID | Material Pathway | Gardner Color | Acid # |
|---|---|---|---|
| 9016-76 | OCD-128 + PE + FASCAT 2003 + Irganox 1010 | 12.9 | 10.1 |
| 9016-80 | TOR + 1,4-CHDM + Rosinox → time → + TOFA | 1.8 | <12 |

TABLE 16

Comparative properties of exemplary plasticizers.

| Lab NB# | Plasticizer | Viscosity @ 350° F. (CPS) | Mettler Softening Point (° C.) | 180° Peel-SS (LBF) | Loop Tack (Lbf) | SAFT (° C.) | Static Shear (1" × 1", 1000 Grams) |
|---|---|---|---|---|---|---|---|
| 9014-0040 | Calsol 5550 | 17,325 | 123.1 | 3.9 | 5.0 | 109.3 | 8290 |
| 9023-0031 | 9016-0076 | 13,200 | 116.8 | 3.5 | 5.3 | 100.5 | 2,282 |
| 9023-0037 | 9016-0080 | 14,650 | 102 | 6.1 | 6 | 99.3 | 10,000+ |

Of particular importance is the increased peel and loop found with the 9016-0080 material combined with the higher levels of static shear (cohesive strength). Traditionally plasticizers do not augment adhesion or strength so this combination is intriguing and may offer unique adhesive performance. The low color and low odor of the 9016-0080 makes it particularly useful for applications/markets like non-woven where these properties, while aesthetic in nature are required.

Table 17 shows the adhesive formulations of the compounds of the present invention and commercial raw materials in generic tape example. Table 18 shows the adhesive formulations of the compounds of the present invention and commercial raw materials in generic label formulation.

Table 19 shows the physical property performance of the formulations of Table 17 in the generic tape adhesive. Table 20 shows the physical property performance of the formulations of Table 18 in the generic label formulation.

TABLE 17

Adhesive formulations-Generic Tape example.

| Sample ID | Example Adhesive | Example 2 Adhesive | Example 3 Adhesive | Example 4 Adhesive | Example 5 Adhesive | Competitive 1 Adhesive | Competitive 2 Adhesive | Compettive 3 Adhesive |
|---|---|---|---|---|---|---|---|---|
| Example 1 | 15 | | | | | | | |
| Example 2 | | 15 | | | | | | |
| Example 3 | | | 15 | | | | | |
| Example 4 | | | | 15 | | | | |
| Exaraple 5 | | | | | 15 | | | |
| Competitive Example 1 | | | | | | 15 | | |
| Competitive Example 2 | | | | | | | 15 | |
| Competitive Example 3 | | | | | | | | 15 |
| BNX 1037 | 0.5 | 0.5 | 0.5 | 0.5 | 0.5 | 0.5 | 0.5 | 0.5 |
| Escorez 1310LC | 48.5 | 48.5 | 48.5 | 48.5 | 48.5 | 48.5 | 48.5 | 48.5 |
| Vector 4113A | 36 | 36 | 36 | 36 | 36 | 36 | 36 | 36 |

TABLE 18

Adhesive formulations - Generic Label formulation.

| Sample ID | Example 3 label Adhesive | Competitive 2 Adhesive | Competitive 3 Adhesive | Example 4 Adhesive |
|---|---|---|---|---|
| Example 3 | 14.5 | | | |
| Competitive 2 | | 14.5 | | |
| Competitive 4 | | | 14.5 | |
| Competitive 5 | | | | 14.5 |
| BNX 1037 | 0.5 | 0.5 | 0.5 | 0.5 |
| Wingtack Extra | 35 | 35 | 35 | 35 |
| Westez 5300 | 22 | 22 | 22 | 22 |
| KRATON D1118 | 18 | 18 | 18 | 18 |
| KRATON D1117 | 10 | 10 | 10 | 10 |

TABLE 19

Comparative properties of exemplary adhesives.

| Adhesive Sample ID | Diluent used | Viscosity @ 177° C. (cPs) | Mettler Softening Point (° C.) | 180° Peel-SS (Lbf) | Loop Track (Lbf) | SAFT (° C.) | Static Shear (minutes) 0.5 × 1 |
|---|---|---|---|---|---|---|---|
| Example 1 Adhesive | Example 1 | 10,100 | 103.2 | 1.4 | 2.5 | 93.2 | 95 |
| Example 2 Adhesive | Example 2 | 12,000 | 109.1 | 2.7 | 3.4 | 92.4 | 123 |
| Example 3 Adhesive | Example 3 | 19,266 | 116.7 | 6.1 | 7.2 | 104.5 | 3920 |
| Example 4 Adhesive | Example 4 | 9,575 | 105.2 | 4.1 | 6.1 | 93.9 | 625 |
| Example 5 Adhesive | Example 5 | 7,125 | 99.6 | 7.0 | 6.8 | 91.6 | 483 |
| Competitive 1 Adhesive | Competitive Sample 1 | 4,320 | 102.1 | 2.6 | 4.2 | 95.0 | 382 |
| Competitve 2 Adhesive | Competitive Sample 2 | 20,300 | 126 | 4.3 | 5.6 | 113.9 | 1,888 |
| Competitive 3 Adhesive | Competitive sample 3 | 24,600 | 126.0 | 4.6 | 2.0 | 104.7 | 2,369 |

TABLE 20

Comparative properties of exemplary adhesives.

| Sample ID | Diluent Used | Viscosity @ 177° C. (cPs) | Mettler Softening Point (° C.) | SAFT (° C.) | Static Shear (minutes) 0.5 × 1 | 180° Peel-HDPE (% FT) | 180° Peel on 99% Recycled Currugate (% Fiber Tear) |
|---|---|---|---|---|---|---|---|
| Example 3 Label Adhesive | Example 3-Label | 3,250 | 91.7 | 83.6 | 8,597 | 78 | 94 |
| Competitive 2 Adhesive | Competitive Sample 2-Label | 2,860 | 95.9 | 90.9 | 3,811 | 45 | 29 |
| Competitive 3 Adhesive | Competitive Sample 4 | 2,935 | 97.1 | 88 | 2,206 | 16 | 20 |
| Example 4 Adhesive | Competitive Sample 5 | 2,850 | 103.5 | 88.7 | 1,894 | 9 | 24 |

Adhesive formulations comprising the plasticizers as described herein demonstration improved performance.

In certain aspects, the description provides methods and assays for performing comparisons of the properties of adhesive formulations as described herein versus adhesive formulations prepared using adhesive industry standard plasticizers. For example, adhesive properties such as viscosity @ 177° C., mettler softening point (° C.), 180° peel-ss (Lbf), loop tack (Lbf), SAFT (° C.) and static shear (minutes) 0.5×1 were compared when the said adhesives were formulated as generic tape adhesives. Adhesive properties such as viscosity @ 177° C., mettler softening point (° C.), SAFT (° C.), static shear (minutes) 0.5×1, 180° peel-HDPE (% FT) and 180° peel on 99% recycled corrugate (% fiber tear) were compared when the said adhesives were formulated as generic lable adhesives.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

The contents of all references, patents, pending patent applications and published patents, cited throughout this application are hereby expressly incorporated by reference.

Those skilled in the art will recognize, or be able to ascertain using no more than routine experimentation, many equivalents to the specific embodiments of the invention described herein. Such equivalents are intended to be encompassed by the following claims. It is understood that the detailed examples and embodiments described herein are given by way of example for illustrative purposes only, and are in no way considered to be limiting to the invention. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present invention will be apparent from the appended claims. Moreover, those skilled in the art will recognize, or be able to ascertain using no more than routine experimentation, many equivalents to the specific embodiments of the invention described herein. Such equivalents are intended to be encompassed by the following claims.

The invention claimed is:
1. An adhesive plasticizer comprising:
    (i) an ester of a tall oil fatty acids (TOFA) and a polyhydric alcohol,
    (ii) an ester of a tall oil rosin (TOR), a tall oil fatty acids (TOFA), and a polyhydric alcohol, or
    (iii) a combination thereof.
2. The adhesive plasticizer of claim 1, wherein the tall oil fatty acids (TOFA) is a modified tall oil fatty acids (TOFA), the tall oil rosin (TOR) is a modified tall oil rosin, or a combination thereof.
3. The adhesive plasticizer of claim 1, wherein the plasticizer comprises TOFA:Glycerine:TOR, TOFA:Trimethylolpropane:TOR, TOFA:diethylene glycol:TOR, TOFA:pentaerythritol, TOFA: pentaerythritol:adipic acid, hydrogenated rosin acid: 1,4-cyclohexanedimethanol:stearic acid, branched fatty acid: pentaerythritol, stearic acid: 1,4-cyclohexanedimethanol:disproportionated rosin, TOFA:D-sorbitol, oleic acid:1,4-cyclohexanedimethanol:TOR, TOFA:1,4-butanediol:TOR, TOFA:1,4-benzenedimethanol: TOR, TOFA:bis[4-(2-hydroxyethoxy)phenyl]sulfone:TOR, or combinations thereof.
4. An adhesive formulation comprising at least one of the adhesive plasticizer of claim 1.
5. The adhesive formulation of claim 4, wherein the formulation further comprises at least one of an antioxidant, a tackifier, or a copolymer.
6. The adhesive formulation of claim 4, wherein the formulation comprises an effective amount of the adhesive plasticizer to enhance at least one property selected from the group consisting of decreased viscosity, increased workability, increased peel, increased loop tack, increased adhesion, increased static shear, and increased cohesion.
7. The adhesive formulation of claim 5, wherein the antioxidant comprises a phosphite antioxidant, a phosphate, a phosphonite antioxidant, a thioether antioxidant, a phenolic antioxidant, a hindered aromatic amine, a butylated hydroxytoluene or a combination thereof.
8. The adhesive formulation of claim 5, wherein the tackifier comprises rosins, natural rosins, modified rosins, hydrogenated rosins, glycerol esters of natural rosins, glycerol esters of modified rosins, pentaerythritol esters of natural rosins, pentaerythritol esters of modified rosins, pentaerythritol esters of hydrogenated rosins, copolymers of natural terpenes, three-dimensional polymers of natural terpenes, hydrogenated derivatives of copolymers of hydrogenated terpenes, polyterpene resins, hydrogenated derivatives of phenol-based modified terpene resins, aliphatic petroleum hydrocarbon resins, hydrogenated derivatives of aliphatic petroleum hydrocarbon resins, aromatic petroleum hydrocarbon resins, hydrogenated derivatives of aromatic petroleum hydrocarbon resins, cyclic aliphatic petroleum hydrocarbon resins, hydrogenated derivatives of cyclic aliphatic petroleum hydrocarbon resins or a combination thereof.
9. The adhesive formulation of claim 5, wherein the copolymer comprises ethylene-vinyl acetate (EVA), ethylene-acrylate, polyolefins, polybutene-1, amorphous polyolefin, polyamides, polyesters, polyurethanes, styrene block copolymers (SBC), polycaprolactone, polycarbonates, fluoropolymers, silicone rubbers, polypyrrole (PPY), styrene-butadiene-styrene (SBS), styrene-butadiene-rubber (SBR), styrene-ethylene/butylene-styrene (SEBS), styrene-ethylene/propylene (SEP), styrene-isoprene-butylene copolymers (SIBS), styrene-ethylene/propylene-styrene copolymers (SEPS), styrene-isoprene-styrene (SIS), vinyl ethers, conjugated diene compound, vinyl-based aromatic hydrocarbon, hydrogenated conjugated diene-based polymer, non-hydrogenated conjugated diene-based polymer or a combination thereof.
10. The adhesive formulation of claim 5, further including an additional plasticizer comprising medicinal white oils, naphthenic mineral oils, adipates, polypropylene oligomers, polybutene oligomers, polyisoprene oligomers, hydrogenated polyisoprene and/or polybutadiene oligomers, benzoate esters, vegetable or animal oils and their derivatives, sulfonic acid esters, mono alcohols, polyhydric alcohols, polyalkylene glycols having a molecular weight of 200 to 6000 g/mol, hydrocarbon oils, polybutene/polyisoprene oligomers, hydrogenated naphthenic oils, or combinations thereof.
11. The adhesive formulation of claim 5, wherein the adhesive is a hot melt pressure sensitive adhesive.
12. The adhesive formulation of claim 5, wherein the adhesive is a hygienic adhesive.
13. The adhesive plasticizer of claim 1, wherein the molar ratio of acid to alcohol is from about 0.5:1 to about 1.2:1.
14. The adhesive formulation of claim 4, wherein the plasticizer comprises from about 5 to about 50 wt % of the total weight of the formulation.
15. A method of preparing plasticizer comprising (i) an ester of a tall oil fatty acids (TOFA) and a polyhydric alcohol, (ii) an ester of a tall oil rosin (TOR), a tall oil fatty acids (TOFA), and a polyhydric alcohol, or (iii) a combination thereof, the method comprising:
    a) heating (i) a tall oil fatty acid acids (TOFA) or (ii) tall oil fatty acids (TOFA) and tall oil rosin (TOR) under nitrogenous conditions;
    b) admixing and stirring in 1,4-cyclohexanedimethanol (CHDM) with heat followed by addition of at least one catalyst;
    c) allowing the mixture to reach reaction temperature and reacting to a predetermined acid value;
    d) allowing reaction to reach a lower temperature and adding tall oil fatty acids (TOFA), a tall oil rosin (TOR), or a combination thereof;
    e) reheating the mixture to desired reaction temperature until a desired acid number value is achieved; and
    f) recooling the mixture and adding at least one antioxidant.
16. The adhesive formulation of claim 5, wherein the plasticizer comprises TOFA:Glycerine:TOR, TOFA:TOR: Trimethylolpropane:TOR, TOFA:diethylene glycol:TOR, TOFA:pentaerythritol, TOFA:pentaerythritol:adipic acid, hydrogenated rosin acid:1,4-cyclohexanedimethanol: stearic acid, branched fatty acid: pentaerythritol, stearic acid: 1,4-cyclohexanedimethanol:disproportionated rosin, TOFA:D-sorbitol, oleic acid:1,4-cyclohexanedimethanol:TOR, TOFA:1,4-butanediol:TOR, TOFA:1,4-benzenedimethanol: TOR, TOFA:bis[4-(2-hydroxyethoxy)phenyl]sulfone:TOR, or combinations thereof.
17. The adhesive plasticizer of claim 1, further comprising an ester of a polyhydric alcohol and a tall oil rosin (TOR).
18. The adhesive formulation of claim 10, wherein the polyalkylene glycols having a molecular weight of 200 to 6000 g/mol is polypropylene glycol or polybutylene glycol.

* * * * *